United States Patent [19]

Tibbals

[11] Patent Number: 4,846,167
[45] Date of Patent: Jul. 11, 1989

[54] ANTI-DISCONNECT DEVICE

[76] Inventor: James R. Tibbals, 2565 Sherhill Dr., Mississauga, Ontario, Canada, L5J 3Z2

[21] Appl. No.: 31,553

[22] Filed: Mar. 30, 1987

[51] Int. Cl.⁴ .............................................. A62B 9/04
[52] U.S. Cl. .............................. 128/202.27; 285/236; 128/912
[58] Field of Search ................... 128/201.13, 202.27, 128/203.13, 912, 911; 604/904; 285/236, 252, 332, 417, 31, 32

[56] References Cited

U.S. PATENT DOCUMENTS

| | | | |
|---|---|---|---|
| 562,963 | 6/1896 | Horner | 285/236 |
| 3,228,714 | 1/1966 | Dricken | 285/236 |
| 3,667,781 | 6/1972 | Holbrook | 128/912 |
| 3,874,712 | 4/1975 | Watson | 285/236 |
| 4,119,334 | 10/1978 | Steed | 285/236 |
| 4,457,543 | 7/1984 | Justus | 285/236 |
| 4,483,556 | 11/1984 | LiVolsi | 285/236 |
| 4,538,839 | 9/1985 | Ledgerwood | 285/236 |
| 4,578,855 | 4/1986 | Van Der Hagen | 285/236 |
| 4,596,246 | 6/1986 | Lyall | 128/205.12 |
| 4,699,404 | 10/1987 | Drevs | 285/236 |

FOREIGN PATENT DOCUMENTS 0009594 of 1906 United Kingdom ............... 285/236

*Primary Examiner*—Max Hindenburg
*Assistant Examiner*—John P. Lacyk
*Attorney, Agent, or Firm*—Eugene J. A. Gierczak

[57] ABSTRACT

A device for releasably securing and sealing the connectable ends of first and second conduits in a breathing circuit, comprising; a flexible tube manipulatively slidable over the connectable ends of the first and second conduits so as to frictionally embrace the ends of the first and second conduits and releasable secure and seal the conduits against dislodgement and leakage, a first clamp presented at one end of the flexible tube for releasably clamping one end of the flexible tube to the first conduit, a projection extending outwardly from the first clamp and adapted to be embedded in the flexible tube.

10 Claims, 2 Drawing Sheets

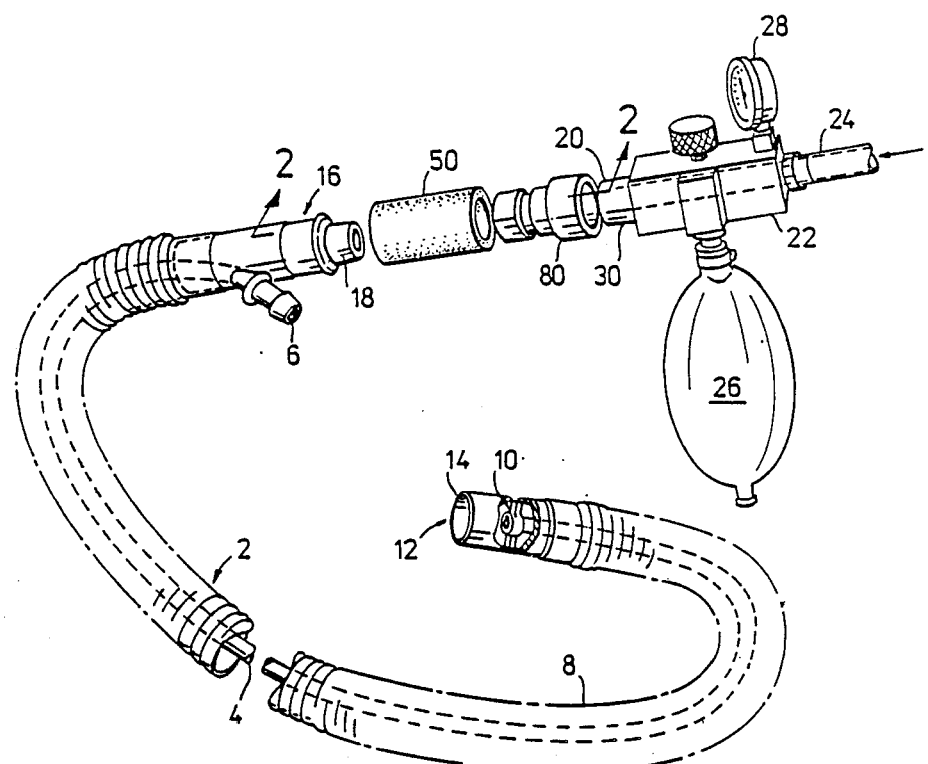
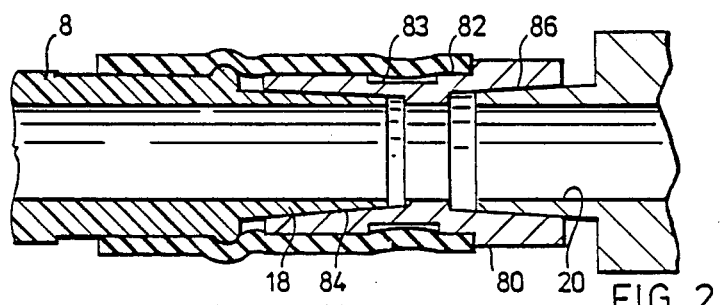
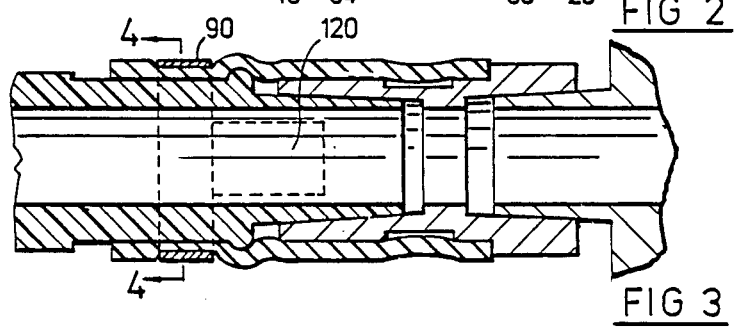

ANTI-DISCONNECT DEVICE

FIELD OF INVENTION

This invention relates to a device for releasably securing and sealing the connectable ends of conduits in a breathing circuit, and in particular, relates to an assembly for connecting a co-axial circuit to a co-axial mount in a Bain circuit configuration.

BACKGROUND TO THE INVENTION

Various means have heretofore been employed in order to connect the ends of pipes or conduits. For example, U.S. Pat. No. 796,220 discloses a threadless pipe coupling while U.S. Pat. No. 793,103 illustrates a hose pipe coupling.

Breathing apparatus also include hoses or conduits which direct the flow of breathing gases. In this regard, U.S. Pat. No. 4,385,629 teaches a portable emergency respiratory system which include flexible tubes which interfit with one another in a relatively snug-relation.

Medical equipment such as anesthetic breathing apparatus utilize conduits to deliver oxygen with anesthetic gases and vapours to a patient during surgical procedures performed on the patient.

It is important that the conduits in such breathing equipment are properly connected. There is, however, a danger of inadvertant disconnection between such conduits which may lead to drastic results to the patient (such as brain damage or death) if such condition is unnoticed.

Connecting systems for ventilator and anestethic gas machines have heretofore been developed in an attempt to prevent unintended disconnection. In particular, U.S. Pat. No. 4,557,261 discloses a connection system for ventilators or anestethic gas machines having spring-biased fastening members. Such connection system present a relatively complicated device requiring a relatively costly assemblage of the constituent parts.

Moreover, there has been a recent trend to utilize the Bain circuit configuration in anesthetic breathing circuitry. In this regard U.S. Pat. No. 4,596,246 teaches that in the Bain circuit, the inspiratory and expiratory hoses or conduits are co-axial. In a typical Bain circuit, fresh gas is delivered through the innermost co-axial hose to the distal end of the hose for inspiration by the patient. The outer, larger diameter hose, which surrounds the fresh gas delivery hose serves to warm the inspired gases in the inspiratory conduit and as a fresh gas reservoir containing some fresh gas for inspiration by the patient and as an expiratory channel for communicating gas exhaled by the patient to the exhaust-scavenging portion of the circuit.

The Bain circuit configurations which are presently being utilized do not employ devices for securing such conduits against dislodgment or for sealing such conduits against inadvertant leakage.

It is an object of this invention to utilize an improved device for releasably securing and sealing the ends of conduits in a breathing circuit which present a relatively simple construction that is easily manufactured.

Another object of this invention resides in utilizing an assembly for connecting a co-axial anesthetic breathing circuit to a co-axial mount.

Yet another object of this invention is to provide an improved locking and sealing device which provides tactile as well as visual confirmation of the locking component status.

FEATURES OF THE INVENTION

The broadest aspect of this invention relates to a device for releasably securing and sealing the connectable ends of first and second conduits in a breathing circuit, comprising; a flexible tube manipulatively slidable over the connectable ends of said first and second conduits so as to frictionally embrace the ends of said first and second conduits and releasably secure and seal said conduits against dislodgement and leakage, a first clamp presented at said one end of said flexible tube for releasably clamping said one end of such flexible tube to said end of said first conduit, said first clamp including a projection extending outwardly from said first clamp and adapted to be embedded in said flexible tube.

Another aspect of this invention relates to an assembly for connecting a co-axial anesthetic breathing circuit to a co-axial mount comprising; an expiratory conduit presenting at one end thereof a tappered male connector; an inspiratory conduit co-axially mounted within the expiratory conduit; said inspiratory conduit adapted to receive breathing and anesthetic gases and said expiratory conduit adapted to vent said breathing and anesthetic gases; a co-axial mount presenting a tapered male connection at one end thereof for receiving said vented gases; a connecting conduit having an outer cylindrical surface, with an inner surface presenting, a first tapered female connector at one end thereof adapted to receive said tapered male connector of said expiratory conduit for releasable frictional engagement therebetween, a second tapered female connector at the other end thereof adapted to receive said tapered male connector of said mount and releasably secured thereto; a flexible tube manipulatively slidable over said outer surface of said connecting conduit and said expiratory conduit so as to frictionally embrace said ends of said connecting conduit and expiratory conduit and secure and seal said conduits against dislodgement and leakage; a first clamp presented at one end of said flexible tube for releasably clamping said one end of said flexible tube to said expiratory conduit; a second clamp presented at said other end of said flexible tube for releasably clamping said other end of said flexible tube to said connecting conduit a connecting strip for connecting the first clamp to the second clamp.

DRAWINGS OF THE INVENTION

FIG. 1 is a partial exploded perspective view of a Bain anesthetic breathing circuit.

FIG. 2 is a cross-sectional view taken along the lines 2—2 of FIG. 1.

FIG. 3 is a cross-sectional view of a second embodiment of the invention taken along the lines 2—2 of FIG. 1.

DESCRIPTION OF THE INVENTION

Figure 4:
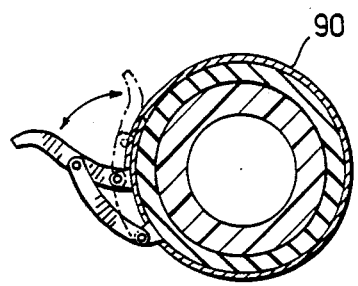
FIG. 4 is a cross-sectional view taken along the lines 4—4 of FIG. 3.

Identical parts have been given identical numbers throughout the figures.

FIG. 1 illustrates an anesthetic breathing circuit 2 which is well known to those persons skilled in the art as having a co-axial configuration, more specifically identified as Mapleson "D" circuit, as popularized by Dr. Bain and known to persons skilled in the art as a Bain configuration.

The anesthetic breathing circuit includes an inspiratory conduit 4 which is adapted to receive breathing gases and anesthetic gases through inlet port 6. The inspiratory conduit 4 is co-axially mounted within expiratory conduit 8 as illustrated in FIG. 1. Conduits 8 and 4 are typically fabricated from plastic materials.

The distal end 10 of inspiratory conduit 4 is suitably attached to the distal end 12 of expiratory conduit 8 in a well known fashion as illustrated in FIG. 1, and therefore shall not be described herein.

The distal end 12 of expiratory conduit 8 presents a tapered male/female connector 14 which is adapted to receive an endotracheal tube (not shown) which is inserted into the patient's trachea via the mouth or nose to provide an adequate airway during surgical procedures. As the patient inhales, breathing gases and anesthetic gases are drawn through the inspiratory conduit 4 and out the distal end 10. As the patient exhales the exhausted gases are vented through expiratory conduit 8 to the proxmal end 16 of expiratory conduit 8.

The proxmal end 16 of the co-axial circuit 2 presents a tapered nozzle or tapered male connector 18 which in the prior art is adapted to be fitted within a tapered hole or tapered female connector 20 located in the co-axial mount 22. The co-axial mount 22 includes a conduit 24 which is adapted to receive the vented breathing and anesthetic gases. The Bain co-axial mount 22 also includes breathing bag 26, pressure gauge 28, as well as a pressure relief valve mechanism (which has not been shown as such mechanism does not form part of the invention).

In the prior art, the tapered male connector 18 is received by tapered female connector 20 and is retained therein by a friction tapered fit. Such connection is susceptible to unintentional or accidental disconnection which may have lethal results to the patient.

The connected ends of expiratory conduit 8 and co-axial mount 22 may be secured against dislogement by utilizing a flexible tube 50. However, a typical Bain mount 22 has a very short tapered outer surface or male connector 30 and a connecting conduit 80 is utilized herein in order to present the flexible tube 50 from slipping off an outer surface 30.

As best illustrated at FIG. 2, connecting conduit 80 presents a outer surface 82 which may be cylindrical or slightly tapered, and an inner surface presenting a first tapered female connector or opening 84 at one end thereof adapted to receive the tapered male connector 18 of expiratory conduit 80 for releasable frictional engagement therebetween.

The connecting conduit 80 also presents a second tapered female connector 86 at the other end thereof adapted to receive the tapered male connector 30 of Bain co-axial mount 22 and is releasably secured thereto by the tapered frictional fit. Glue or a set screw may also be utilized to more fixedly secure the connecting conduit 80 to Bain mount 22.

The connecting conduit 80 provides a cylindrical recessed outer surface 83 against which flexible tube 50 may bear against without slipping off as would be the case if flexible hose 50 were to be applied over tapered male connector 30 of Bain mount 22.

Flexible tube 50 may be comprised of suitable material such as silicon or the like.

Flexible tube 50 is manipulatively slideable over the outer cylindrical surface 82 of connecting conduit 80 and the expiratory conduit 8 so as to frictionally embrace said ends of the connecting conduit 80 and expiratory conduit 8 and secure such conduits against dislodgement. Furthermore, since flexible tube 50 embraces such ends of conduits 80 and 8, tube 50 seals such ends against leakage even in the event when the tapered male connector 18 becomes cracked or broken. Such tapered male connectors are easily cracked or broken while they are attached in the Bain mount when subjected to a slight lateral force sufficient to crack or break the connector.

FIG. 3 illustrates another embodiment of the invention whereby a clamp 90 is presented at one end or distal end of the flexible tube 50 for releasably clamping said one end of the flexible tube 50 to the expiratory conduit 8.

Figure 6:
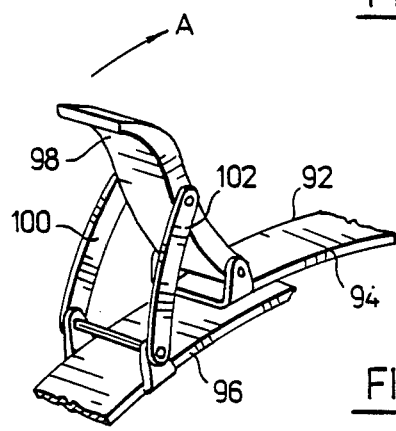
FIG. 6 is a partial perspective view of the clamping mechanism.

The clamp 90 is more fully illustrated in FIGS. 4 and 6. such clamp 90 includes a band 92 which is adapted to circumfrentially embrace the flexible tube 50. The ends 94 and 96 of band 92 are attached by means of a toggle handle 98 and arms 100 and 102. Moving handle 98 in the direction of arrow A causes the ends 94 and 96 of the bank 92 to be further drawn and overlapped together so as to clamp the flexible tube 50 to expiratory conduit 8.

Figure 5:
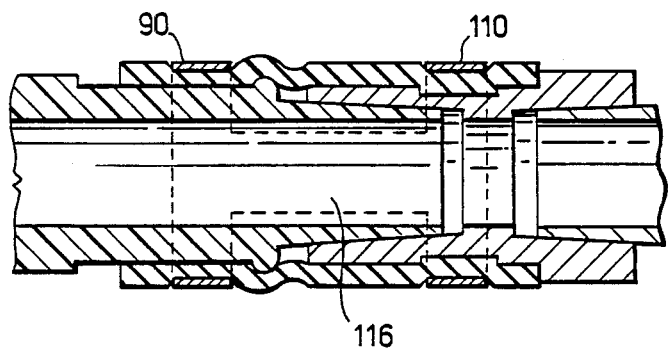
FIG. 5 is a cross-sectional view of a third embodiment of the invention taken along the lines 2—2 of FIG. 1.

FIG. 5 illustrates yet another embodiment of the invention whereby a second clamp 110 (which is identical to first clamp 90) is presented at the other end of the flexible tube 50 for releasably clamping the other end of the flexible tube 50 to connecting conduit 8.

FIG. 5 also illustrates the use of a connecting bridge or member 116 which comprises a piece of material that integrally connects clamp 90 to second clamp 110. First clamp 90, second clamp 110, and connecting bridge 116 are embedded within flexible tube 50 as best illustrated in FIG. 5.

FIG. 3 also illustrates the use of a leg 120 or projection extending outwardly from said clamp 90 which is adapted to be embedded in flexible tube 50 when only one clamp 90 is utilized.

Although the invention has been described in association with the connected ends of a Bain configuration the device as described herein may be utilized to secure and seal the connectable ends of conduits in other types of ventilator circuits or breathing circuits. Such device would comprise a flexible tube manipulatively slideable over the connectable ends of first and second conduit so as to frictionally embrace said ends of the first and second conduits and releasably secure and seal the conduits against dislodgement and leakage.

While the form of the invention shown and described herein is admirably adapted to fulfill the objects primarily stated, it is to be understood that it is not intended to confine the invention to the form or embodiment disclosed herein, for it is susceptible of embodiment in various other forms within the scope of the appended claims.

The embodiments of the invention in which an exclusive property or privilege is claimed are defined as follows:

1. In a device for releasably securing and sealing axially interconnectable ends of first and second conduits in a breathing circuit, comprising; a flexible tube manipulatively slidable over said axially interconnectable ends of said first and second conduits so as to frictionally embrace said axially interconnected ends of said first and second conduits and releasably secure and seal said conduits against dislodgement and leakage, first clamping means presented at said one end of said flexible tube for releasably clamping said one end of said flexible tube to said end of said first conduit, said first clamping means including a projection means extending axially outwardly from said first clamping means from said first conduit to said second conduit, said projection means adapted to be embedded in said flexible tube to further strengthen the device to resist breaking or cracking of the conduits due to a lateral 2. In a device as claimed in claim 1 including a second clamping means presented at the other end of said flexible tube for releaseably clamping said other end of said flexible tube to said end of said second conduit.

3. In a device as claimed in claim 2 wherein said projection means extends axially from said first clamping means to said second clamping means so as to integrally connect said first clamping means and said second clamping means.

4. In a device as claimed in claim 3 wherein said projection means comprises a strip of material.

5. In a device as claimed in claim 4 wherein said clamping means and said projection means are embedded in said flexible tube.

6. In a device as claimed in claim 5 wherein said flexible means comprises silicon material.

7. In an assembly for connecting a co-axial anesthetic breathing circuit to a co-axial mount comprising:
   (a) expiratory conduit means presenting at one end thereof a tapered male connector;
   (b) inspiratory conduit means co-axially mounted within said expiratory conduit means;
   (c) said inspiratory conduit means adapted to receive breathing and anesthetic gases, and said expiratory conduit means adapted to vent said breathing and anesthetic gases;
   (d) a co-axial mount presenting a tapered male connector at one end thereof for receiving said vented gases;
   (e) a connecting conduit having an outer cylindrical surface, with an inner surface presenting;
   (i) a first tapered female connector at one end thereof adapted to axially interconnectably receive said tapered male connector of said expiratory conduit means for releasable frictional engagement therebetween;
   (ii) a second tapered female connector at the other end thereof adapted to axially interconnectably receive said tapered male connector of said mount and releasable secured thereto;
   (f) a flexible tube manipulatively slidable over said outer surface of said connecting conduit and said expiratory conduit so as to frictionally embrace said axially interconnectable ends of said connecting conduit and expiratory conduit and secure and seal said conduits against dislodgement and leakage;
   (g) a first clamping means presented at one end of said flexible tube for releasably clamping said one end of said flexible tube to said expiratory conduit;
   (h) a second clamping means presented at said other end of said flexible tube for releasably clamping said other end of said flexible tube to said connecting conduit.
   (i) connecting means for connecting first clamping means to second clamping means, said connecting means extending generally axially in the region adjacent said axially interconnectable ends of said connecting conduit and expiratory conduit said connecting means further strengthens the device to resist breaking or cracking of the expiratory conduit due to a lateral force.

8. An assembly as claimed in claim 7 wherein said connecting means is integrally connected to said first and second clamping means.

9. An assembly as claimed in claim 8 wherein said connecting means comprises a piece of material that integrally connects said first and second clamping means.

10. An assembly as claimed in claim 9 wherein said first clamping means, said second clamping means and said connecting means are embedded within said flexible tube.

* * * * *